US011015169B2

(12) United States Patent
Hasegawa et al.

(10) Patent No.: US 11,015,169 B2
(45) Date of Patent: May 25, 2021

(54) CULTURE MEDIUM FOR PLURIPOTENT STEM CELLS

(71) Applicant: Kyoto University, Kyoto (JP)

(72) Inventors: Kouichi Hasegawa, Kyoto (JP); Shinya Yasuda, Kyoto (JP); Hosein Shahsavarani, Kyoto (JP); Noriko Yoshida, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/128,747

(22) PCT Filed: Mar. 25, 2015

(86) PCT No.: PCT/JP2015/059104
§ 371 (c)(1),
(2) Date: Sep. 23, 2016

(87) PCT Pub. No.: WO2015/147047
PCT Pub. Date: Oct. 1, 2015

(65) Prior Publication Data
US 2017/0114322 A1 Apr. 27, 2017

(30) Foreign Application Priority Data
Mar. 26, 2014 (JP) .............................. JP2014-064174

(51) Int. Cl.
C12N 5/0735 (2010.01)
C12N 5/074 (2010.01)
(52) U.S. Cl.
CPC ......... C12N 5/0606 (2013.01); C12N 5/0696 (2013.01); C12N 2500/25 (2013.01); C12N 2500/38 (2013.01); C12N 2500/90 (2013.01); C12N 2501/00 (2013.01); C12N 2501/04 (2013.01); C12N 2501/602 (2013.01); C12N 2501/603 (2013.01); C12N 2501/604 (2013.01); C12N 2501/606 (2013.01); C12N 2501/608 (2013.01); C12N 2501/727 (2013.01); C12N 2501/73 (2013.01); C12N 2501/999 (2013.01); C12N 2506/1307 (2013.01); C12N 2510/00 (2013.01)
(58) Field of Classification Search
None
See application file for complete search history.

(56) References Cited

U.S. PATENT DOCUMENTS

2008/0194021 A1* 8/2008 Mays .................... C12N 5/0607
435/375
2011/0263016 A1* 10/2011 Rancourt ............. C12N 5/0606
435/366

FOREIGN PATENT DOCUMENTS

| WO | 2007016485 A2 | 2/2007 |
| WO | 2007113505 A2 | 10/2007 |
| WO | 2008/133904 A1 | 11/2008 |
| WO | 2010035136 A2 | 4/2010 |
| WO | 2011019953 A1 | 2/2011 |
| WO | 2012019122 A2 | 2/2012 |

OTHER PUBLICATIONS

Dakic et al., Harmine stimulates proliferation of human neural progenitors, PeerJ, 2016, 4:e2727, pp. 1-13.*
PubChem, Tacrolimus, pp. 1-29, retrieved from the internet: https://pubchem.ncbi.nlm.nih.gov/compound/tacrolimus_monohydrate, Mar. 5, 2018.*
StemCell Technologies, ID-8 DYRK pathway inhibitor, retrieved from the internet Mar. 5, 2018: https://www.stemcell.com/id-8.html.*
Kunick et al., Bioroganic & Medicinal Chemistry Letters 14 (2004) 413-416 (Year: 2004).*
Anguera et al., "Molecular Signatures of Human Induced Pluripotent Stem Cells Highlight Sex Differences and Cancer Genes," Cell Stem Cell 11, Jul. 6, 2012, pp. 75-90.
Beers et al., "Passaging and colony expansion of human pluripotent stem cells by enzyme-free dissociation in chemically defined culture conditions," Nature Protocols, vol. 7, No. 11, 2012, pp. 2029-2040.
Chen et al., "Chemically defined conditions for human iPSC derivation and culture," Nature Methods, vol. 8, No. 5, May 2011, pp. 424-429 and online methods (2 pages).
Hasegawa et al., "Wnt Signaling Orchestration with a Small Molecule DYRK Inhibitor Provides Long-Term Xeno-Free Human Pluripotent Cell Expansion," Stem Cells Translational Medicine 2012; 1:18-28.
Lessing et al., "X Chromosome Inactivation and Epigenetic Responses to Cellular Reprogramming," Annu. Rev. Genom. Hum. Genet. 2013, 14:85-110.
Myrianthopoulos et al., "Novel Inverse Binding Mode of Indirubin Derivatives Yields Improved Selectivity for DYRK Kinases," ACS Med. Chem. Lett. 2013, 4, pp. 22-26.
Ronen et al., "Sex-Dependent Gene Expression in Human Pluripotent Stem Cells," Cell Reports, 8, Aug. 21, 2014, pp. 923-932.
Sato et al., "Maintenance of pluripotency in human and mouse embryonic stem cells through activation of Wnt signaling by a pharmacological GSK-3-specific inhibitor," Nature Medicine, vol. 10, No. 1, Jan. 2004, pp. 55-63.
International Search Report issued in related application PCT/JP2015/059104, dated Oct. 1, 2015, 2 pages.
International Preliminary Report on Patentability issued in related application PCT/JP2015/059104, dated Apr. 14, 2016, 4 pages.
Sokol, Sergei Y., "Maintaining embryonic stem cell pluripotency with Wnt signaling," Development, 2011, vol. 138, No. 20, pp. 4341-4350.

(Continued)

Primary Examiner — Scott Long
Assistant Examiner — Evelyn Y Pyla
(74) Attorney, Agent, or Firm — McNeill Baur PLLC

(57) ABSTRACT

An object of the present invention is to provide a medium that comprises fewer protein components and enables the maintenance of pluripotent stem cells in an undifferentiated state. The culture medium for pluripotent stem cells comprises a GSK3β inhibitor (A) and a DYRK inhibitor (B).

14 Claims, 9 Drawing Sheets

(56) References Cited

OTHER PUBLICATIONS

Shen, Weijun, et al., "Inhibition of DYRK1A and GSK3B induces human β-cell proliferation," Nature Communications, 2015, vol. 6 No. 8372, pp. 1-11.

Extended European Search Report issued in EP Application No. 15768143.8, dated Nov. 27, 2017, 8 pages.

Bellmaine S, et al., "Inhibition of DYRK1A Disrupts Neural Lineage Specification in Human Pluripotent Stem Cells," eLife 6:e24502 (2017), 20 pages.

Davidson K, et al., "Wnt/β-Catenin Signaling Promotes Differentiation, Not Self-Renewal, of Human Embryonic Stem Cells and is Repressed by Oct4," PNAS 109(12):4485-4490 (2012).

Dravid G, et al., "Defining the Role of Wnt/β-Catenin Signaling in the Survival, Proliferation, and Self-Renewal of Human Embryonic Stem Cells," Stem Cells 23(10):1489-1501 (2005).

Hasegawa K, et al., "A Method for the Selection of Human Embryonic Stem Cell Sublines with High Replating Efficiency After Single-Cell Dissociation," Stem Cells 24(12):2649-2660 (2006).

Hasegawa K, et al., "Wnt Signaling Orchestration with a Small Molecule DYRK Inhibitor Provides Long-Term Xeno-Free Human Pluripotent Cell Expansion," Stem Cells Transl Med. 1(1):18-28 (2012), Epub Dec. 7, 2011.

Higuchi Y, et al., "Specific Direct Small Molecule p300/β-Catenin Antagonists Maintain Stem Cell Potency," Curr Mol Pharmacol. 9(3):272-279 (2016).

Space Daily, "Culturing cheaper stem cells," available at https://www.spacedaily.com/reports/Culturing_cheaper_stem_cells_999.html, 2 pages (Mar. 7, 2018).

Pelobiotech.com, "Kyoto University Found Way of Culturing Stem Cells More Cost-Effective," available at https://www.pelobiotech.com/kyoto-university-found-way-of-culturing-stem-cells-more-cost-effective/, 5 pages (Mar. 6, 2018).

Adil, M.M., Schaffer, D.V., "Cheaper and less variable expansion," Nat Biomed Eng 2, 144-145 (2018), https://doi.org/10.1038/s41551-018-0209-y.

Sanchez-Arillas, "Bringing Human Induced Pluripotent Stem Cell Culture to the Masses," BC Regenerative Medicine Initiative, available at https://bcregmed.ca/bringing-human-induced-pluripotent-stem-cell-culture-to-the-masses, 4 pages (Apr. 2018).

Yasuda, Sy. et al., "Chemically defined and growth-factor-free culture system for the expansion and derivation of human pluripotent stem cells," Nat Biomed Eng 2, 173-182 (2018), https://doi.org/10.1038/s41551-018-0200-7.

Phys.org, "Culturing cheaper stem cells," available at https://phys.org/news/2018-03-culturing-cheaper-stem-cells.html, 2 pages (Mar. 6, 2018).

* cited by examiner

CULTURE MEDIUM FOR PLURIPOTENT STEM CELLS

This application is the national phase entry pursuant to 35 U.S.C. § 371 of International Application No. PCT/JP2015/059104, filed Mar. 25, 2015, which claims the benefit of priority to Japanese Patent Application No. 2014-064174, filed Mar. 26, 2014, both of which are incorporated herein by reference in their entirety.

TECHNICAL FIELD

The present invention relates to a culture medium for pluripotent stem cells that does not contain serum or a differentiation-suppressing protein, but enables the maintenance of pluripotent stem cells in an undifferentiated state.

BACKGROUND ART

For their pluripotency and proliferation potency, pluripotent stem cells, such as iPS cells and ES cells, are expected for use in cell transplantation treatments, drug discovery, and the like, or as a tool to study diseases. Pluripotent stem cells, when in the presence of serum or factors appropriate for the cells, are usually capable of self-replication while almost indefinitely maintaining an undifferentiated state. As appropriate factors for human pluripotent stem cells, for example, differentiation-suppressing proteins, such as bFGF and TGFβ, have been reported. However, these differentiation-suppressing proteins are generally very expensive, and a large amount thereof is required to maintain an undifferentiated state; thus, the use of pluripotent stem cells is significantly hindered in terms of cost.

Further, pluripotent stem cells are required to have uniform properties when applied to cell transplantation; therefore, as a medium component, it is desirable to use a minimum amount of proteins whose properties are highly likely to vary from lot to lot.

Under such circumstances, there have recently been reports regarding a medium (E8 medium) comprising only four types of proteins, bFGF, TGFβ, insulin, and transferrin (Non-patent Literature (NPL) 1, Non-patent Literature (NPL) 2, and Patent Literature (PTL) 1), and a medium comprising only three types of proteins, Wnt, insulin, and transferrin (Non-patent literature (NPL) 3 and Patent Literature (PTL) 2).

However, these two media still contain bFGF, TGFβ, Wnt, and the like, which are generally very expensive, and media that can be prepared at a lower cost are thus in demand. Additionally, the growth of cells is relatively slow in the latter medium, requiring a larger volume of the medium to obtain a certain number of cells.

CITATION LIST

Patent Literature

PTL 1: WO 2012/019122
PTL 2: WO 2011/019953

Non-Patent Literature

NPL 1: Chemically defined conditions for human iPSC derivation and culture. Chen G, Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M, Thomson J A, Nature Methods. 2011 May; 8 (5): 424-9.
NPL 2: Passaging and colony expansion of human pluripotent stem cells by enzyme-free dissociation in chemically defined culture conditions. Beers J, Gulbranson D R, George N, Siniscalchi L I, Jones J, Thomson J A, Chen G, Nature Protocol. 2012 November; 7 (11): 2029-40.
NPL 3: Wnt signaling orchestration with a small molecule DYRK inhibitor provides long-term xeno-free human pluripotent cell expansion. Hasegawa K, Yasuda S Y, Teo J L, Nguyen C, McMillan M, Hsieh C L, Suemori H, Nakatsuji N, Yamamoto M, Miyabayashi T, Lutzko C, Pera M F, Kahn M, Stem Cells Translational Medicine. 2012 January; 1(1): 18-28.

SUMMARY OF INVENTION

Technical Problem

An object of the present invention is to provide a medium that contains fewer protein components and enables the maintenance of pluripotent stem cells in an undifferentiated state. Another object of the present invention is to provide a medium that is prepared at a lower cost. Still another object of the present invention is to provide a medium in which pluripotent stem cells are more efficiently grown.

Solution to Problem

As a result of extensive research, the present inventors found that the combined use of a GSK3β inhibitor and a DYRK inhibitor as medium components solves the above problems. The present inventors also found that a further use of an NFAT inhibitor in combination enables more efficient growth of pluripotent stem cells. The present inventors conducted further research based on these findings, and have accomplished the present invention.

More specifically, the present invention encompasses the following embodiments:

Item 1. A culture medium for pluripotent stem cells, the medium comprising a GSK3β inhibitor (A) and a DYRK inhibitor (B).
Item 2. The medium according to Item 1, which is free from serum.
Item 3. The medium according to Item 1 or 2, which is free from a differentiation-suppressing protein.
Item 4. The medium according to any one of Items 1 to 3, comprising only insulin and transferrin as protein components.
Item 5. The medium according to any one of Items 1 to 4, wherein the component (A) is at least one member selected from the group consisting of 1-azakenpaullone, kenpaullone, and CHIR99021.
Item 6. The medium according to any one of Items 1 to 5, wherein the component (A) is 1-azakenpaullone.
Item 7. The medium according to any one of Items 1 to 6, wherein the component (B) is at least one member selected from the group consisting of ID-8, harmine, and indirubin analogs.
Item 8. The medium according to any one of Items 1 to 7, wherein the component (B) is ID-8.
Item 9. The medium according to any one of Items 1 to 8, further comprising an NFAT inhibitor (C).
Item 10. The medium according to Item 9, wherein the component (C) is tacrolimus.
Item 11. The medium according to any one of Items 1 to 10, for culture in the absence of feeder cells.

Item 12. The medium according to any one of Items 1 to 11, wherein the pluripotent stem cells are from primates.

Item 13. A method for culturing pluripotent stem cells, the method using the medium of any one of Items 1 to 12.

Item 14. A differentiation-suppressing agent for pluripotent stem cells, the agent comprising a GSK3β inhibitor (A) and a DYRK inhibitor (B).

Advantageous Effects of Invention

The present invention provides a medium that enables the maintenance of pluripotent stem cells in an undifferentiated state over a long period of time, even without using serum or a differentiation-suppressing protein. Thus, the medium of the present invention is prepared very inexpensively, compared with existing media that contain, as essential components, serum or differentiation-suppressing proteins.

The properties of proteins are usually highly likely to vary from lot to lot. However, the present invention, which uses fewer protein components, provides a medium with less variation in properties between lots. The present invention is thus suitable for use in cell transplantation and the like that require pluripotent stem cells with uniform properties.

The medium of the present invention enables the growth of pluripotent stem cells at an efficiency comparable to or higher than that of existing media. This makes it possible to prepare a certain number of pluripotent stem cells at a lower cost.

The medium of the present invention enables the maintenance of cells in an undifferentiated state and the growth of cells, even in the absence of feeder cells, to an extent comparable to that in the presence of feeder cells. Additionally, this medium may be used not only for adhesion culture, but also for suspension culture.

DESCRIPTION OF EMBODIMENTS

Figure 1:
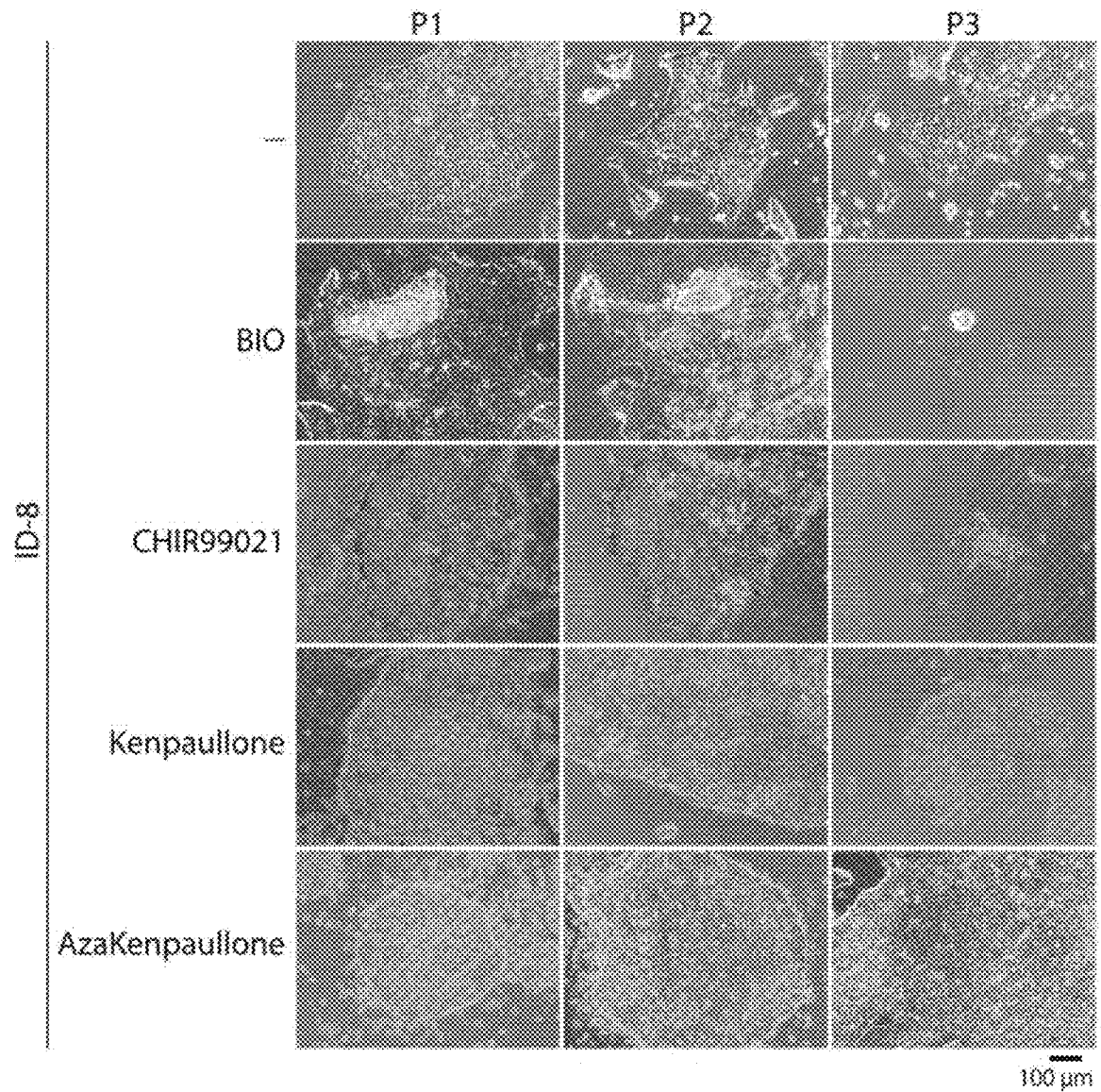
FIG. 1 shows images of the cells observed in Example 1.

The following describes a culture medium for pluripotent stem cells (hereinafter sometimes abbreviated as "the medium of the present invention") comprising a GSK3β inhibitor (A) (hereinafter sometimes referred to as "the component (A)") and a DYRK inhibitor (B) (hereinafter sometimes referred to as "the component (B)"), and a method for culturing pluripotent stem cells using this medium (hereinafter sometimes abbreviated as "the culture method of the present invention").

Component (A) and Component (B)

The GSK3β inhibitor is not particularly limited as long as it is a compound that acts to inhibit GSK3β (glycogen synthase kinase-3β) or as long as it is a compound known to be used to inhibit GSK3β. The term "inhibit" as used herein means not only to inhibit the enzymatic function of GSK3β, but also to reduce the amount of intracellular expression of GSK3β. This term preferably means to inhibit the enzymatic function of GSK3β. Specific examples of GSK3β inhibitors include 1-azakenpaullone, kenpaullone, CHIR99021, BIO, CID 5706819, 9-cyanopaullone, ML320, AR A014418, SB216763, SB415286, A 1070722, lithium chloride, staurosporine, GSK-3β inhibitor VI, GSK-3β inhibitor X, GSK-3β inhibitor XV, aloisine A, MeBIO, alsterpaullone, 5-iodo-indirubin-3'-monoxime, 10Z-hymenialdisine, TWS 119 ditrifluoroacetate, indirubin-5-sulfonic acid sodium salt, Ro-31-8220, manzamine A, IM-12, CESI, 3F8, TC-G 24, TCS 2002, L803, and the like.

Of these, from the viewpoint of achieving more stable maintenance of an undifferentiated state or more efficient cell growth, the GSK3β inhibitors may be those that inhibit the enzymatic function of GSK3β and have an $IC_{50}$ against GSK3β of, for example, 100 nM or less, preferably 50 nM or less, more preferably 30 nM or less, still more preferably 25 nM or less, and furthermore preferably 5 to 25 nM. Additionally, from the same viewpoint, GSK3β-specific inhibitors may also be used that inhibit the enzymatic function of GSK3β and have an $IC_{50}$ against, for example, an enzyme other than GSK3β (e.g., GSK3a) of 5 nM or more, preferably 10 nM or more, more preferably 25 nM or more, still more preferably 50 nM or more, furthermore preferably 100 nM or more, and still furthermore preferably 1 μM or more. $IC_{50}$ values against each enzyme are known information and publicly disclosed on websites of, for example, commercially available GSK30 inhibitors (e.g., selleckchem.com and scbt.com). More specifically, for example, it is possible to use 1-azakenpaullone, kenpaullone, CHIR99021, BIO, and the like; preferably 1-azakenpaullone, kenpaullone, CHIR99021, and the like; more preferably 1-azakenpaullone, kenpaullone, and the like; and still more preferably 1-azakenpaullone and the like. These may be commercially available products, or may be those synthesized in accordance with known information.

The component (A) may be used alone, or in a combination of two or three or more.

The DYRK inhibitor is not particularly limited as long as it is a compound that acts to inhibit DYRKs (dual-specificity tyrosine-phosphorylation-regulated kinases), or as long as it is a compound known to be used to inhibit DYRKs. The term "inhibit" as used herein means not only to inhibit the enzymatic function of DYRKs, but also to reduce the amount of intracellular expression of DYRKs. This term preferably means to inhibit the enzymatic function of DYRKs. DYRKs encompass several types of enzymes. For example, human DYRKs encompass five enzymes with similar kinase domains, i.e., DYRK1A, DYRK1B, DYRK2, DYRK3, and DYRK4. Of these, as a DYRK inhibitor, a DYRK1A and/or DYRK1B inhibitor is preferable, and a DYRK1A- and/or DYRK1B-specific inhibitor is more preferable. Specifically, DYRK inhibitors may be ID-8, harmine, indirubin analogs, TG003, INDY, L41, PROINDY, SB 216763, chronogen quinolinus, leucettine, Cyclacell limited pyrimidines, quinazoline, Compound 35, 7BIO, 6BIO, indirubin, A2191, ML315, ML320-Compound 35, 36d, SEL141, and the like. Of these, from the viewpoint of achieving more stable maintenance of an undifferentiated state or more efficient cell growth, ID-8, harmine, indirubin analogs, INDY, and the like are preferable; ID-8, harmine, and the like are more preferable; and ID-8 and the like are still more preferable. As indirubin analogs, for example, compounds disclosed in 6i (716) or 6e (713) in American Chemical Society, Lett, 2014, 4, 22-26 are preferable, and compounds disclosed in 6i (716) of this document are more preferable. These may be commercially available products, or may be those synthesized in accordance with known information.

The component (B) may be used alone, or in a combination of two or three or more.

According to the present invention, it is possible to maintain pluripotent stem cells in an undifferentiated state over a long period of time with the combined use of the component (A) and component (B), without the use of serum or a differentiation-suppressing protein. This indicates that the combined use of the component (A) and component (B) acts to suppress differentiation. Therefore, the component (A) and component (B) may be used in combination as a differentiation-suppressing agent for pluripotent stem cells.

Culture Medium for Pluripotent Stem Cells

The medium of the present invention comprises a combination of the component (A) and the component (B).

The concentration of the component (A) in the medium differs depending on the type of the component (A), and is, for example, 10 to 3000 nM, preferably 50 to 2000 nM, more preferably 200 to 1500 nM, still more preferably 350 to 1000 nM, and furthermore preferably 450 to 850 nM. More specifically, the following are examples of the concentration ranges of, for example, 1-azakenpaullone, kenpaullone, and CHIR99021 in the medium.

1-Azakenpaullone: for example 10 to 3000 nM, preferably 100 to 2500 nM, more preferably 250 to 2000 nM, still more preferably 400 to 1500 nM, and furthermore preferably 500 to 1000 nM;

Kenpaullone: for example 10 to 3000 nM, preferably 50 to 2000 nM, more preferably 100 to 1500 nM, still more preferably 200 to 1000 nM, and furthermore preferably 250 to 750 nM; and CHIR99021: for example 10 to 3000 nM, preferably 50 to 2000 nM, more preferably 100 to 1500 nM, still more preferably 200 to 1000 nM, and furthermore preferably 250 to 750 nM.

The concentration of the component (B) in the medium differs depending on the type of the component (B), and is, for example, 10 to 4000 nM, and preferably 200 to 3000 nM. More specifically, the following are examples of the concentration ranges of, for example, ID-8, harmine, and an indirubin analog in the medium.

ID-8: for example 10 to 3000 nM, preferably 50 to 2000 nM, more preferably 100 to 1500 nM, still more preferably 200 to 1000 nM, and furthermore preferably 250 to 750 nM;

Harmine: for example 300 to 6000 nM, preferably 600 to 5000 nM, more preferably 1000 to 3000 nM, still more preferably 1500 to 2500 nM; and Indirubin analog: for example 10 to 3000 nM, preferably 50 to 2000 nM, more preferably 100 to 1500 nM, still more preferably 200 to 1000 nM, and furthermore preferably 250 to 750 nM.

The medium of the present invention is usually prepared by mixing a basal medium with the component (A) and component (B).

The basal medium is not particularly limited as long as it is usable as a basal medium for culture of pluripotent stem cells, and usually contains magnesium, calcium, potassium, zinc, iron, and like standard inorganic salts, buffering agents, glucose, vitamins, essential amino acids, and the like. Specific examples include Dulbecco's modified Eagle's medium (DMEM), minimal essential medium (MEM), basal medium eagle (BME), RPMI1640, F-10, F-12, α-minimal essential medium (αMEM), Glasgow's minimal essential medium (GMEM), Iscove's modified Dulbecco's medium (IMDM), and the like. Of these, DMEM/F-12 is preferable.

The basal medium may further contain a buffering agent, such as HEPES, a nonessential amino acid, an antioxidant agent, and the like. Examples of nonessential amino acids include L-glutamine, L-alanine, L-asparagine, L-aspartic acid, L-glutamine acid, glycine, L-proline, L-serine, and the like, with L-glutamine and the like being preferable. Examples of antioxidant agents include ascorbic acid, 2-mercaptoethanol, dithiothreitol, and the like, with ascorbic acid and the like being preferable. The concentrations of these components may be adjusted to known concentrations that are used in culture of pluripotent stem cells.

From the viewpoint of achieving more efficient pluripotent stem cell growth, the medium of the present invention preferably further contains an NFAT inhibitor (C) (hereinafter abbreviated as "the component (C)").

The NFAT inhibitor is not particularly limited as long as it is a compound that acts to inhibit NFAT (nuclear factor of activated T-cells) or calcineurin, or as long as it is a compound known to be used to inhibit NFAT or calcineurin. The term "inhibit" as used herein means not only to inhibit the enzymatic function of NFAT or calcineurin, but also to reduce the amount of intracellular expression of NFAT or calcineurin. This term preferably means to inhibit the enzymatic function of NFAT or calcineurin. Specifically, NFAT inhibitors may be tacrolimus (FK506), cyclosporin A, AM404, UR-1505, CN585, sirolimus (rapamycin), endothall, FMPP, tyrphostins, VIVIT 480402, INCA (1, 2, 6), Lie120, Roc-1, NCI3, thiopental, ST1959 (DL111-IT), quercetin, tropisetron, trifluoperazine, PD144795, norcantharidin, ascomycin (FKBP12) and the like. Of these, from the viewpoint of achieving more stable maintenance of an undifferentiated state or more efficient cell growth, tacrolimus and the like are preferable. These may be commercially available products, or may be those synthesized in accordance with known information.

The component (C) may be used alone, or in a combination of two or three or more.

The concentration of the component (C) in the medium differs depending on the type of the component (C), and is, for example 10 to 3000 μM, preferably 50 to 2000 μM, more preferably 100 to 1500 µM, still more preferably 200 to 1000 µM, and furthermore preferably 250 to 750 µM.

The medium of the present invention may contain a differentiation-suppressing protein, serum, or a serum alternative component, if necessary.

The differentiation-suppressing proteins are not particularly limited as long as they are a factor that acts to maintain pluripotent stem cells in an undifferentiated state, or as long as they are a factor known to be used to maintain pluripotent stem cells in an undifferentiated state. Examples include bFGF, TGFβ superfamily members (e.g., activin and nodal), LIF, Wnt, and the like. The concentration of differentiation-suppressing protein may be adjusted to a known concentration that is used in culture of pluripotent stem cells. The differentiation-suppressing proteins may be used alone, or in a combination of two or three or more.

In general, these differentiation-suppressing proteins are very expensive, and the variation of the properties between lots is larger than that of compounds. Since the medium of the present invention comprises a combination of the component (A) and component (B), the medium of the present invention, without using these differentiation-suppressing proteins, enables efficient maintenance of pluripotent stem cells in an undifferentiated state. Accordingly, From the perspective of reducing the cost of preparing the medium, or from the perspective of reducing the variation of the properties of the medium between lots, preferably, the medium of the present invention dose not contain a differentiation-suppressing protein, or preferably, when the medium of the present invention is used, a differentiation-suppressing protein dose not added to the medium of the present invention.

The serum is not particularly limited as long as it is usable in culture of pluripotent stem cells. Examples include fetal bovine serum (FBS) and the like. The concentration of serum may be adjusted to a known concentration that is used in culture of pluripotent stem cells. The serum may be used alone, or in a combination of two or three or more.

In general, serum is expensive, and the variation of the properties between lots is large. Without using serum, the medium of the present invention enables efficient maintenance of pluripotent stem cells in an undifferentiated state, and enables growth of cells. Accordingly, From the perspective of reducing the cost of preparing the medium, or from the perspective of reducing the variation of the properties of the medium between lots, preferably, the medium of the present invention dose not contain serum, or preferably, when the medium of the present invention is used, serum dose not added to the medium of the present invention.

A serum alternative component refers to a component that supports the growth of pluripotent stem cells when added to a serum-free medium. Specific examples include albumins (e.g., bovine serum albumin), albumin alternative additives (e.g., bovine pituitary extract, rice hydrolysate, and fetal bovine albumin, egg albumin, human serum albumin, bovine embryo extract, AlbuMAX I (registered trademark)), transferrin, insulin, and the like. The concentration of serum alternative component may be adjusted to a known concentration that is used in culture of pluripotent stem cells. These serum alternative components may be used alone, or in a combination of two or three or more.

In general, the variation of the properties of protein components is large between lots. Therefore, it is preferable to use minimum types of proteins when used as a serum alternative component. In this respect, the medium of the present invention enables efficient maintenance of pluripotent stem cells in an undifferentiated state, and enables growth of cells, even when the medium comprises only insulin and transferrin as the serum alternative components (or protein components). Therefore, from the viewpoint of further reducing the variation of the properties of the medium between lots, the serum alternative components (or protein components) contained in (or added at the time of culture to) the medium of the present invention are only insulin and transferrin.

In addition to the above, the medium of the present invention may further comprise known components that can be added to a medium for pluripotent stem cells. Of these, from the viewpoint of achieving more efficient cell growth, selenium, ethanolamine, and the like, and preferably selenium and the like, may be used. The concentrations of these components may be adjusted to known concentrations that are used in culture of pluripotent stem cells.

The medium of the present invention may be prepared in either solution or dried form. The medium in a solution form may be provided as a concentrated composition (e.g., 1× to 1000×), and may be appropriately diluted in use. The types of liquid used to dilute or dissolve the composition or medium in a solution or dried form may be easily selected from water, a buffer solution, a physiological saline, and the like, as required.

The pH of the medium of the present invention in a solution form is usually adjusted with a pH adjuster, such as bicarbonate, to 7.0 to 8.2, preferably 7.1 to 7.8, and more preferably 7.2 to 7.5; and the osmotic pressure is adjusted with salts, such as sodium chloride, to 310 to 340 mOsm.

The medium of the present invention is preferably sterilized to prevent contamination. Examples of the sterilization method include UV irradiation, heat sterilization, radial ray irradiation, filtration, and the like.

The medium of the present invention is used as is or with the addition of the above components, if necessary, in culture of pluripotent stem cells (e.g., maintenance of pluripotent stem cells, passage of pluripotent stem cells, and production of induced pluripotent stem cells (iPS cells)).

The pluripotent stem cells to be cultured are not particularly limited as long as they are stem cells having the ability to differentiate into any of three germ layers (endoderm, mesoderm, and ectoderm). The source organism is also not particularly limited, and cells from various animals may be used, including mammals, such as humans, monkeys, mice, rats, hamsters, rabbits, guinea pigs, cows, pigs, dogs, horses, cats, goats, and sheep, as well as birds and reptiles. Of these, it is preferable to use cells from mammals, more preferably primates, still more preferably humans, monkeys, and the like, and furthermore preferably humans. Specific examples of pluripotent stem cells include iPS cells, ES cells, EG cells, EC cells, and the like. As pluripotent stem cells, it is possible to use commercially available products or those deposited, and it is also possible to use those produced in accordance with known methods.

Pluripotent stem cells may be cultured using the medium of the present invention in accordance with standard methods. The following describes a typical passaging procedure and culture conditions. First, grown pluripotent stem cell colonies are rinsed once or twice with PBS; next, a sufficient amount of cell detachment solution is added so as to cover the cell layer, followed by being left to stand for several minutes. A basal medium comprising PBS or serum is added thereto, and cell spheres are dissociated by pipetting. The resulting cell suspension is usually subjected to centrifugation to precipitate cells. After the supernatant is removed, the precipitated cells are resuspended in the medium, and a part thereof is seeded in a dish or in a coated dish covered with feeder cells and cultured at 37° C. in 5% $CO_2$.

When the medium of the present invention is used to produce induced pluripotent stem cells, it is possible to obtain induced pluripotent stem cell colonies in a much more efficient manner than that of a case in which a known culture medium for pluripotent stem cells is used. The phrase "used to produce induced pluripotent stem cells" means that the medium is used as a culture medium for somatic cells to which reprogramming factors have previously been introduced.

As a cell detachment solution, for example, a solution containing EDTA, or a solution containing dispase as an enzyme may be used. A solution containing EDTA is preferable from the viewpoint of achieving higher pluripotent stem cell viability. A solution containing dispase as an enzyme is preferable from the viewpoint of performing passage in simpler manner. The concentration of EDTA or dispase in a cell detachment solution may be determined in accordance with a known concentration used in cell culture.

Examples of the coating components of a coated dish include vitronectin, laminin, and the like. Of these, vitronectin is preferable.

The medium of the present invention is excellent as it enables maintenance of pluripotent stem cells in an undifferentiated state in any of adhesion culture and suspension culture. In adhesion culture, it is possible to stably maintain an undifferentiated state, even in the absence of feeder cells, to an extent comparable to that in the presence of feeder cells. Therefore, from the viewpoint of performing culture in a simpler manner, culture in the absence of feeder cells is preferable.

EXAMPLES

The present invention is described in more detail below, with reference to Examples. However, the present invention is not limited to these Examples.

Example 1: Subculture of Pluripotent Stem Cells Using a Medium Comprising a Gsk3β Inhibitor and a DYRK Inhibitor Preparation of Basal Medium 25 mL of a solution in which a powder DMEM/F-12 medium (D0547, produced by Sigma-Aldrich) had been diluted two-fold with water, 1.4 mL of 6% sodium hydrogen carbonate solution, 0.75 mL of 1 M HEPES solution, 0.045 mL of 0.23 M ascorbic acid solution, 0.9 ML of ITS (Insulin-Transferrin-Selenium: 1 mg/ml-0.55 mg/ml-0.7 μg/ml) solution (ITS-G 41400-045, produced by Life Technologies), and 16.905 mL of water were mixed to obtain 45 mL of basal medium (340 mOsm, pH 7.2 to 7.5).

Preparation of Medium

A GSK3β inhibitor (1-azakenpaullone (A3734, produced by Sigma-Aldrich), kenpaullone (1094-1, produced by BioVision), CHIR99021 (1386, produced by Axon Medchem), or BIO (B1686, produced by Sigma-Aldrich)), and a DYRK inhibitor (ID-8 (11786, produced by Sigma-Aldrich), harmine (Ser. No. 10/010,324, produced by Cayman Chemical), an indirubin analog 716 (6i) (ACS Medicinal Chemistry Letters, 2013, vol. 4, no. 1, pp. 22-26), INDY (405273, produced by Merck Millipore Corporation), L41 (MR-00023, produced by AdipoGen), or TG003 (4336, produced by R&D Systems)) were each added singly or in combination to the basal medium to thereby obtain a medium. The following are final concentrations in the medium.

1-Azakenpaullone: 750 nM;
Kenpaullone: 500 nM;
CHIR99021: 500 nM;
Bio: 1 μM;
ID-8: 500 nM;
Harmine: 2 μM;
Indirubin analog 716: 500 nM;
INDY: 1 μM;
L41: 500 nM; and
TG003: 500 nM.

The obtained medium (hereafter sometimes simply referred to as a "medium") was used in this Example and the following Examples.

Subculture of Pluripotent Stem Cells

Human ES cell lines KhES-1 (provided by Riken BioResource Center) were subcultured in the above medium. More specific details are below. The following culture was performed in the absence of feeder cells in a dish (vitronectin-N-coated dish) in which coating treatment was performed overnight using 1 μg of vitronectin-N (A14700 produced by Life Technologies) per 1 $cm^2$ of the culture dish.

ES cell colonies cultured in accordance with a standard method using a general-purpose medium for human ES cells (20% knockout serum replacement (10828-028, produced by Life Technology), 4 ng/ml of FGF2 (100-18B, produced by Peprotech)/DMEM/F-12 medium (11330-032, produced by Life Technology)) were rinsed once with PBS. A dispase solution (10 mg/ml dispase (Ser. No. 17/105,041, produced by Life Technologies)/DMEM/F-12) was added thereto so as to cover the cells, followed by being left to stand for 5 minutes. The general-purpose medium for human ES cells was added, and the cell spheres were dissociated with pipetting. The obtained cell suspension was subjected to centrifugation (500 cfg, 1 minute) to precipitate the cells. After the supernatant was removed, the precipitated cells were resuspended in the above medium, and about ⅓ thereof was seeded in a vitronectin-N-coated dish and cultured in the above medium at 37° C. in 5% $CO_2$. This passaging procedure was considered to be "P1." The medium was replaced every day or every two days, and the passage was performed every three days or four days (P2, P3, P4, . . . ) as above.

Results

Figure 2:
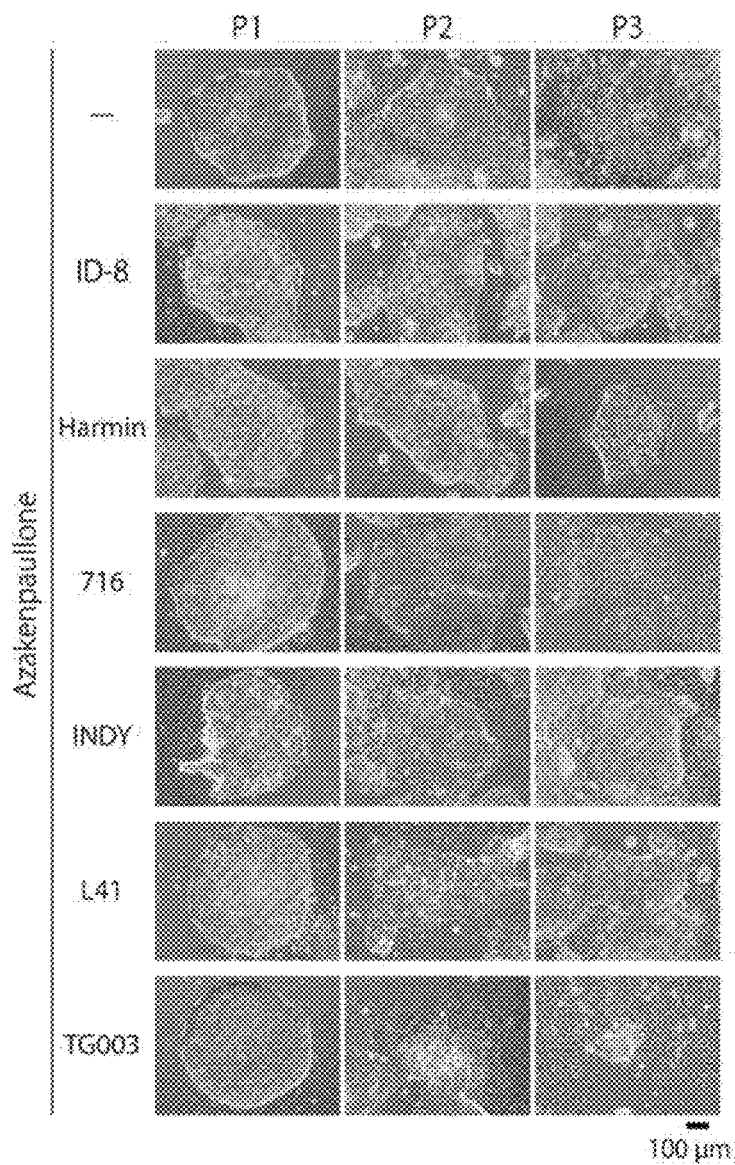
FIG. 2 shows images of the cells observed in Example 1.

FIG. 1 shows images of cells (uppermost row) subcultured using the medium comprising a DYRK inhibitor (ID-8), and images of cells (from the row second from the top to the lowermost row) subcultured using the medium comprising a GSK3β inhibitor (1-azakenpaullone, kenpaullone, CHIR99021, or Bio) and a DYRK inhibitor (ID-8). FIG. 2 shows images of cells (uppermost row) subcultured using the medium comprising a GSK3β inhibitor (1-azakenpaullone), and images of cells (from the row second from the top to the lowermost row) subcultured using the medium comprising a GSK3β inhibitor (1-azakenpaullone) and a DYRK inhibitor (ID-8, harmine, indirubin analog 716, INDY, L41, or TG003). In each figure, P1 shows images of cells taken three days after passage P1. The same applies to P2, P3, and the like.

FIGS. 1 and 2 indicate that a combined use of a GSK3β inhibitor and a DYRK inhibitor enabled the maintenance of the ES cells in an undifferentiated state. Of the GSK3β inhibitors, kenpaullone and 1-azakenpaullone (in particular 1-azakenpaullone) enabled the maintenance of the ES cells in the most stable manner. Of the DYRK inhibitors, ID-8 maintained ES cells in the most stable manner.

Example 2: Role of NFAT Inhibitor in Subculture of Pluripotent Stem Cells

A medium further comprising an NFAT inhibitor (tacrolimus (FK-506) (1007965, produced by Cayman Chemical)), in addition to a GSK3β inhibitor (1-azakenpaullone or kenpaullone) and a DYRK inhibitor (ID-8), was prepared as in Example 1. Using this medium, subculture and cell observation were performed as in Example 1. Separately from this, passage P1 was performed using this medium, as in Example 1, followed by culturing for 6 days without performing passage. Thereafter, the number of the cells was counted in accordance with a standard method, and, based on the counted number of cells, how many times the number of the cells increased within 6 days was calculated.

Results

Figure 3:
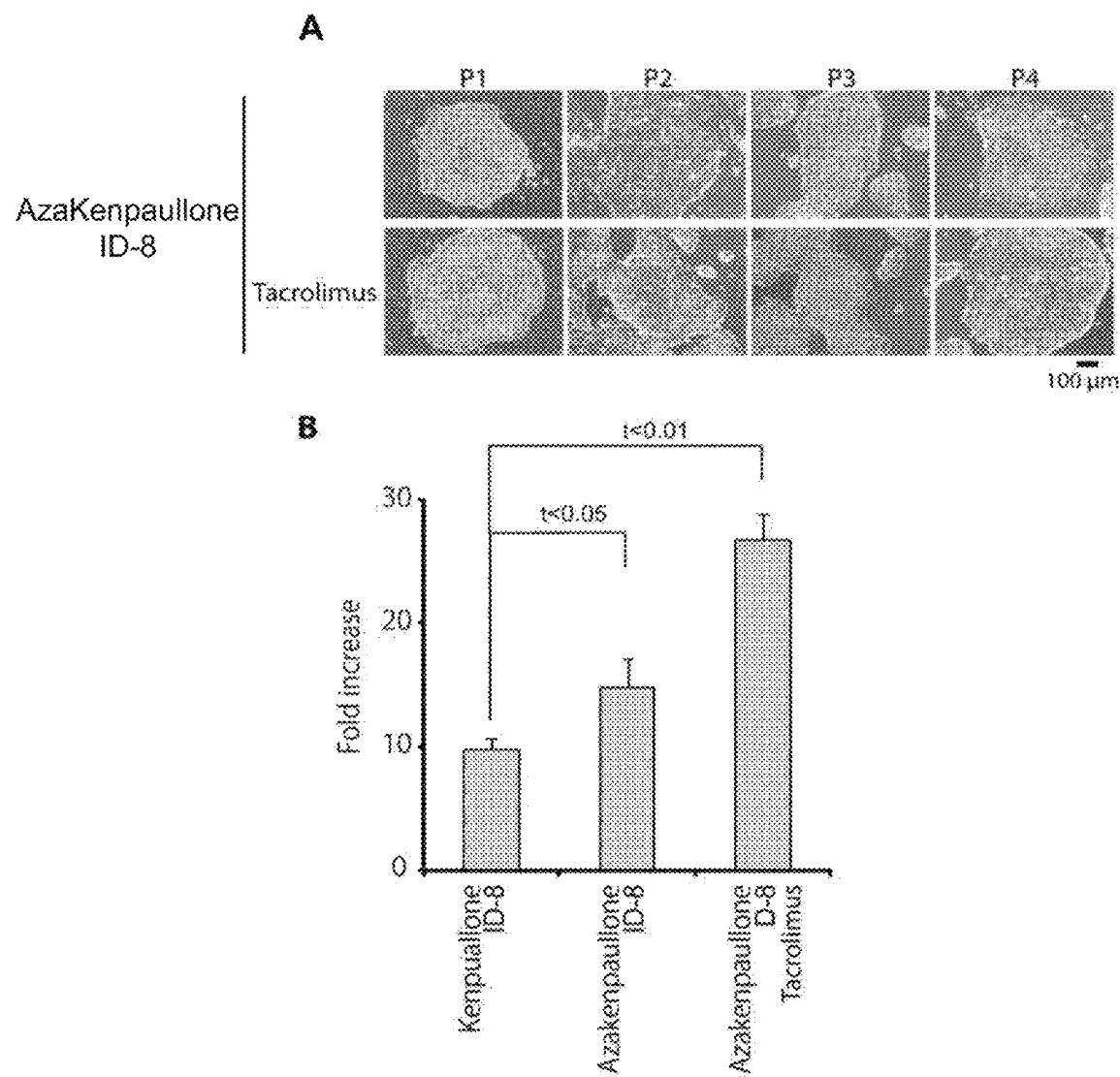
FIG. 3(A) shows images of the cells observed in Example 2.
FIG. 3(B) shows the fold increase of the cells counted in Example 2.

FIG. 3A shows images of the cells, and FIG. 3B show the fold increase of the cells.

FIG. 3A indicates that ES cells are maintained in an undifferentiated state even when an NFAT inhibitor (tacrolimus) is further added, in addition to a GSK3β inhibitor (azakenpaullone) and a DYRK inhibitor (ID-8). Further, FIG. 3B shows that the cell growth is notably accelerated when an NFAT inhibitor (tacrolimus) is added, in addition to a GSK3β inhibitor (azakenpaullone) and a DYRK inhibitor (ID-8). It is also shown that 1-azakenpaullone accelerates the cell growth more than kenpaullone.

Example 3: Long-Term Culture of ES Cells

A medium (medium 1) comprising a GSK3β inhibitor (1-azakenpaullone) and a DYRK inhibitor (ID-8), and a medium (medium 2) further comprising an NFAT inhibitor (tacrolimus) in addition to a GSK3β inhibitor (1-azakenpaullone) and a DYRK inhibitor (ID-8) were prepared as in Example 1. These media were used with human ES cell lines KhES-1, human ES cell lines H9 (W09, provided by WiCell), human iPS cell lines 253G1 (HPS0002, provided by Riken BioResource Center), human iPS cell lines 201B7 (HPS0063, provided by Riken BioResource Center), and human ES cell lines H1 (W01, provided by WiCell) to perform subculture and cell observation, as in Example 1.

Results

Figure 4:
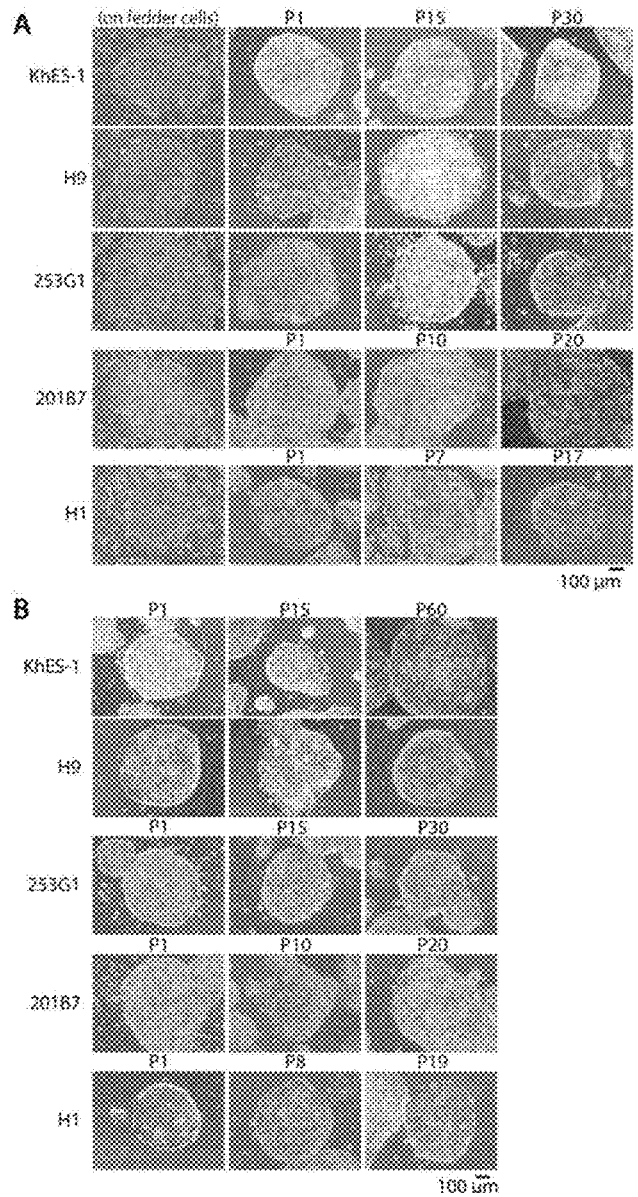
FIG. 4(A) shows images of the cells observed when the medium 1 of Example 3 was used.
FIG. 4(B) shows images of the cells observed when the medium 2 of Example 3 was used.

FIG. 4A shows images of the cells when medium 1 was used. FIG. 4B shows images of the cells when medium 2 was used.

FIGS. 4A and 4B indicate that both media 1 and 2 maintain various pluripotent stem cells in an undifferentiated state over a long period of time (P17 to P60).

ES cells and iPS cells from males are known to be distinguished from ES cells and iPS cells from females in terms of the epigenetic states and gene expression patterns (e.g., Cell Reports (2014) 8: 923-932, Cell Stem Cell (2012) 11(1): 75-90, Annu. Rev. Genomics Hum. Genet. (2013) 14:85-110). In general, possibly due to this fact, it is believed to be more difficult to maintain ES cells and iPS cells from males in an undifferentiated state, compared with ES cells and iPS cells from females. Of the cell lines used in this Example, the human ES cell lines H1 were from males; however, with the use of media 1 and 2, such cells from males were maintained in an undifferentiated state over a long period of time, as in other cells from females (human ES cell lines KhES-1, human ES cell lines H9, human iPS cell lines 253G1, and human iPS cell lines 201B7).

Example 4: Confirmation of Undifferentiated State after Long-Term Culture

Undifferentiated marker expression in the cells after long-term culture of Example 3 was analyzed. The details are below.

Immunostaining

The expression of undifferentiated markers (OCT4, SOX2, NANOG, alkaline phosphatase (ALP), SSEA-3, SSEA-4, TRA1-81, and TRA1-60) in the human ES cell lines KhES-1 maintained up to passage P50 (Example 3), the human iPS cell lines 201B7 maintained up to passage P20 (Example 3), the human ES cell lines H9 maintained up to passage P30 (Example 3), and the human iPS cell lines 253G1 maintained up to passage P20 (Example 3) was detected by immunostaining performed in accordance with a standard method using the medium (Example 3) comprising a GSK3β inhibitor (1-azakenpaullone), a DYRK inhibitor (ID-8), and an NEAT inhibitor (tacrolimus). (The following are the primary antibodies used: OCT4 (Sc-5279, produced by Santa Cruz Biotechnology, 1:200 dilution), SOX2 (Sc-17320, produced by Santa Cruz Biotechnology, 1:100 dilution), NANOG (4903 produced by Cell Signaling Technology, 1:100 dilution), SSEA-3 (Sc-21703 produced by Santa Cruz Biotechnology, 1:50 dilution), SSEA-4 (Sc-59368, produced by Santa Cruz Biotechnology, 1:50 dilution), TRA-1-81 (Sc-21705, produced by Santa Cruz Biotechnology, 1:50 dilution), TRA-1-60 (Sc-21706, produced by Santa Cruz Biotechnology, 1:50 dilution), and alkaline phosphatase (ALP) (VECTOR Blue Alkaline Phosphatase Substrate Kit, SK-5300, produced by VECTOR Laboratories). The secondary antibodies were Alexa Fluor 488 or 594 antibodies, produced by Life Technologies, corresponding to each of the primary antibodies, 1:400 dilution.)

Flow Cytometry

The expression of undifferentiated markers (OCT4, SSEA-4) in the human ES cell lines KhES-1 maintained up to passage P26 (Example 3) and the human ES cell lines H9 maintained up to passage P17 (Example 3) was detected by flow cytometry (BDFACS CANT II, produced by Becton Dickinson) in accordance with a standard method using the medium (Example 3) comprising a GSK3β inhibitor (1-azakenpaullone), a DYRK inhibitor (ID-8), and an NFAT inhibitor (tacrolimus). (The following are the primary antibodies used: OCT4 (Sc-5279, produced by Santa Cruz Biotechnology, 1:100 dilution) and SSEA-4 (Sc-59368, produced by Santa Cruz Biotechnology, 1:100 dilution). The secondary antibodies were Alexa Fluor 488 antibodies produced by Life Technologies corresponding to each of the primary antibodies, 1:1000 dilution.)

Karyotype Analysis

The karyotypes of the human ES cell lines KhES-1 maintained up to passage P49 (Example 3), the human ES cell lines H9 maintained up to passage P33 (Example 3), and the human iPS cell lines 253G1 maintained up to passage P25 (Example 3) were analyzed using a G-band method performed in accordance with a standard method using the medium (Example 3) comprising a GSK3β inhibitor (1-azakenpaullone), a DYRK inhibitor (ID-8), and an NEAT inhibitor (tacrolimus).

Results

Figure 5:
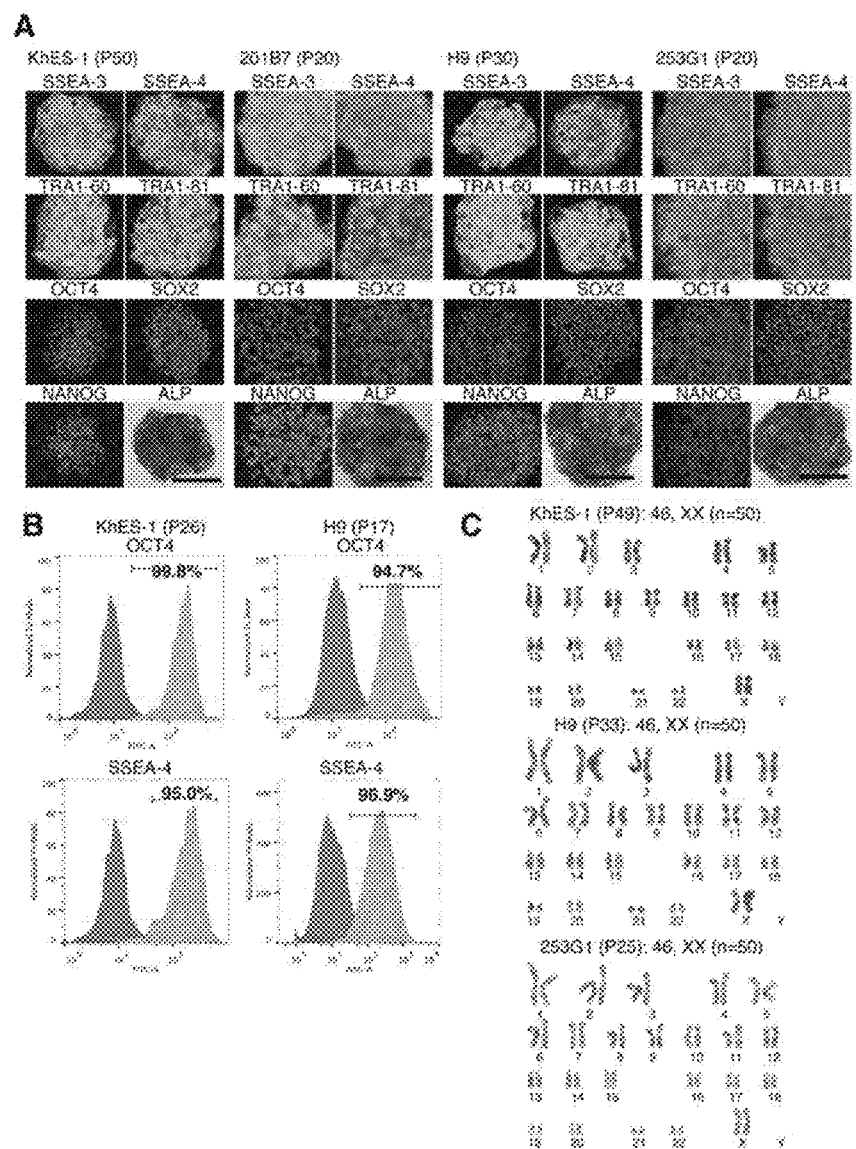
FIG. 5(A) shows the results of immunostaining of Example 4.
FIG. 5(B) shows the results of the flow cytometry of Example 4.
FIG. 5(C) shows the results of the karyotype analysis of Example 4.

FIG. 5A shows the results of immunostaining, FIG. 5B shows the results of flow cytometry, and FIG. 5C shows the results of karyotype analysis. In FIG. 5B, the left-side peaks in the two-dimensional plots represent peaks of negative controls in which the primary antibodies were not used, while the right-side peaks represent peaks in which the primary antibodies were used.

FIGS. 5A and 5B confirm the expression of undifferentiated markers even after the long-term culture. Further, FIG. 5C confirms no change in the karyotypes even after the long-term culture. These results indicate that an undifferentiated state is maintained very stably with the use of a medium comprising a GSK3β inhibitor and a DYRK inhibitor in combination.

Example 5: Comparison with Existing Media

Existing media and the medium (Example 3) comprising a GSK3β inhibitor (1-azakenpaullone), a DYRK inhibitor (ID-8), and an NFAT inhibitor (tacrolimus) were compared in terms of the pluripotent stem cell growth rate and undifferentiated marker expression amount. The details are below.

Preparation of Existing Media

The following were prepared as existing culture media for pluripotent stem cells: an mTeSR1 medium (05850, produced by Stem Cell Technology); an E8 medium (05940, produced by Stem Cell Technology); and a Wnt3A- and ID-8-containing medium. The Wnt3A- and ID-8-containing medium was prepared by adding Wnt3A (315-20 produced by Peprotech) to a final concentration of 10 ng/mL and further adding ID-8 to a final concentration of 500 nM, to the basal medium produced in Example 1.

Measurement of Growth Rate

Human ES cell lines KhES-1 were subcultured using each medium, as in Example 1. The cells were seeded at each passage (every 3 days) so that about 20% of the bottom surface (3.80 cm$^2$) of each well was covered by the cells, and the split at this time was recorded. Passage was performed up to passage P5, and the average split of passages P1 to P5 was calculated.

Detection of Undifferentiated Markers by Flow Cytometry

Human ES cell lines KhES-1 were subcultured using each medium, as in Example 1. The expression of undifferentiated markers (OCT4, SSEA-4) in the cells maintained up to passage P30 was detected by flow cytometry, as in Example 4.

Detection of Undifferentiated Markers by Quantitative PCR

Human ES cell lines KhES-1 were subcultured using each medium, as in Example 1. The expression of undifferentiated markers (OCT4, SSEA-4) in the cells maintained up to passage P5 was detected by quantitative PCR in accordance with a standard method. Separately from this, the undifferentiated markers were also detected in cells (control) that were cultured on feeder cells in a similar manner.

Results

Figure 6:
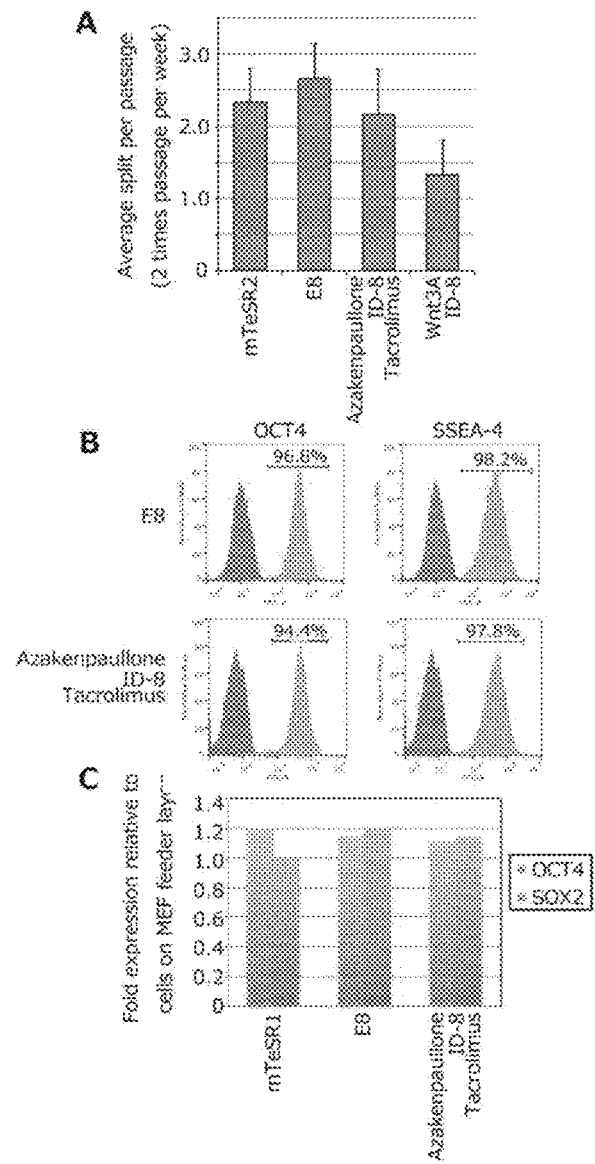
FIG. 6(A) shows the average split per passage as measured in Example 5.
FIG. 6(B) shows the results of the flow cytometry of Example 5.
FIG. 6(C) shows the results of quantitative PCR of Example 5.

FIG. 6A. shows the measurement results of growth rate, FIG. 6B shows the results of undifferentiated marker detection by flow cytometry, and FIG. 6C shows the results of undifferentiated marker detection by quantitative PCR.

FIG. 6A. indicates that the cells in the medium comprising a GSK3β inhibitor (1-azakenpaullone), a DYRK inhibitor (ID-8), and an NFAT inhibitor (tacrolimus) grow at a rate comparable to or faster than that of the cells in existing media. Further, FIGS. 6B and 6C indicate that an undifferentiated state is maintained stably with the use of the medium comprising a GSK3β inhibitor (1-azakenpaullone), a DYRK inhibitor (ID-8), and an NFAT inhibitor (tacrolimus), to an extent comparable to that with the use of existing media; and further, to an extent comparable to that in culture performed on feeder cells.

Example 6: Analysis of Subculture Conditions

Experiment for Consideration of Coating Components of a Dish

Human ES cell lines KhES-1 or human ES cell lines H9 were subcultured, as in Example 1, in a vitronectin-N coated dish, in a dish (Synthemax-coated dish) in which coating treatment was performed overnight using 5 μg of Synthemax (Synthemax (registered trademark) II-SC substrate A14700, produced by Corning) per 1 cm$^2$ of the culture dish, or in a dish (Laminin 511 E8-coated dish) in which coating treatment was performed overnight using 1 μg of Laminin 511 E8 (iMatrix-511 892001, produced by Nippi) per 1 cm$^2$ of the culture dish.

Experiment for Consideration of Cell Detachment Solution

Human ES cell lines KhES-1 or human ES cell lines H9 were subcultured, as in Example 1, using an EDTA solution (0.5 mM EDTA/PBS) or a dispase solution (10 mg/mL dispase/basal medium) as a cell detachment solution used for passage.

Results

Figure 7:
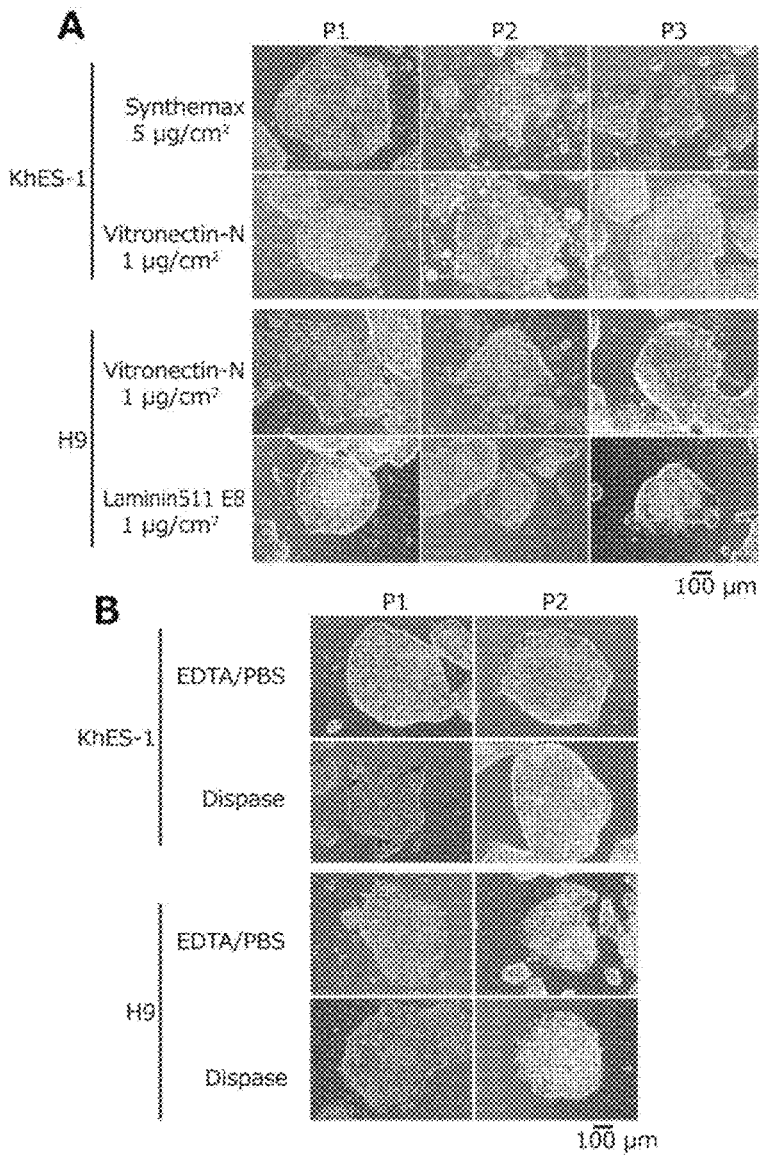
FIG. 7(A) shows images of the cells observed in an experiment for consideration of coating components in Example 6.
FIG. 7(B) shows images of the cells observed in an experiment for consideration of cell detachment solution in Example 6.

FIG. 7A shows images of the cells after the experiment for consideration of coating components, and FIG. 7B shows images of the cells after the experiment for consideration of cell detachment solution.

FIG. 7A indicates that ES cells are maintained in an undifferentiated state even when Synthemax or Laminin 511 E8 is used as a coating component. The vitronectin-N, in particular, maintained ES cells most stably.

FIG. 7B indicates that ES cells are maintained in an undifferentiated state with the use of any of the EDTA solution or dispase solution as a cell detachment solution. When the EDTA solution was used, the passaging procedure was somewhat difficult, although the ES cell viability tended to be high. In contrast, when the dispase solution was used, the cell viability tended to be low, although the passaging procedure was easy.

Example 7: Application to Suspension Culture

Figure 8:
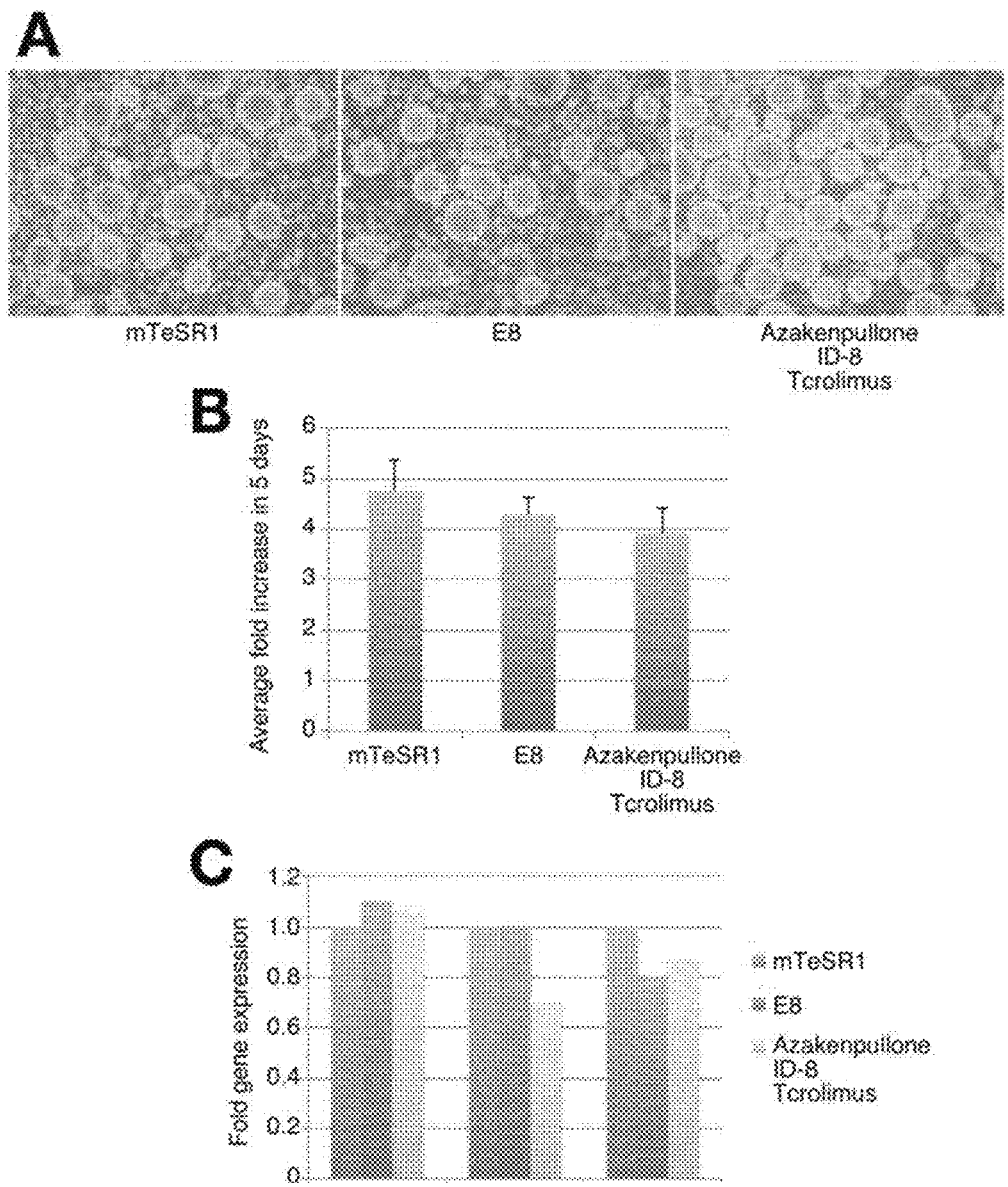
FIG. 8(A) shows images of the cells observed in Example 7.
FIG. 8(B) shows the fold increase of the cells counted in Example 7.
FIG. 8(C) shows the results of quantitative PCR of Example 7.

Human ES cell lines KhES-1 were suspension-cultured in accordance with a standard method using the medium (Example 3) comprising a GSK3β inhibitor (1-azakenpaullone), a DYRK inhibitor (ID-8), and an NFAT inhibitor (tacrolimus); an mTeSR1 medium; or an E8 medium. FIG. 8A shows images of the cells after passage P3.

FIG. 8A indicates that even when suspension culture is performed, ES cells are maintained in an undifferentiated state with the use of the medium comprising a GSK3β inhibitor (1-azakenpaullone), a DYRK inhibitor (ID-8), and an NFAT inhibitor (tacrolimus), as in existing media.

After passage P1, the number of cells was counted in accordance with a standard method after 5-day culture without passaging, and, based on the counted number of cells, how many times the cells increased within 5 days was calculated. FIG. 8B shows the results.

FIG. 8B shows that the growth rate in the suspension culture in the medium comprising a GSK3β inhibitor (1-azakenpaullone), a DYRK inhibitor (ID-8), and an NFAT inhibitor (tacrolimus) is comparable to the growth rate in existing media.

Further, the expression of undifferentiated markers (OCT4, SOX2, NANOG) in the cells maintained up to passage P7 was detected by quantitative PCR performed in accordance with a standard method. FIG. 8C shows the expression amount of each undifferentiated marker as a relative value relative to the expression amount with the use of an mTeSR1 medium.

FIG. 8C shows that the degree of expression of the undifferentiated markers when suspension culture was performed in the medium comprising a GSK3β inhibitor (1-azakenpaullone), a DYRK inhibitor (ID-8), and an NFAT inhibitor (tacrolimus) was comparable to the degree of expression in existing media.

Example 8: Production of iPS Cells iPS cells were produced using the medium (Example 3) comprising a GSK3β inhibitor (1-azakenpaullone), a DYRK inhibitor (ID-8), and an NFAT inhibitor (tacrolimus); or using an E8 medium. Then, the production efficiency, the form of colonies, and the expression of undifferentiated markers were analyzed. The details are below.

Figure 9:
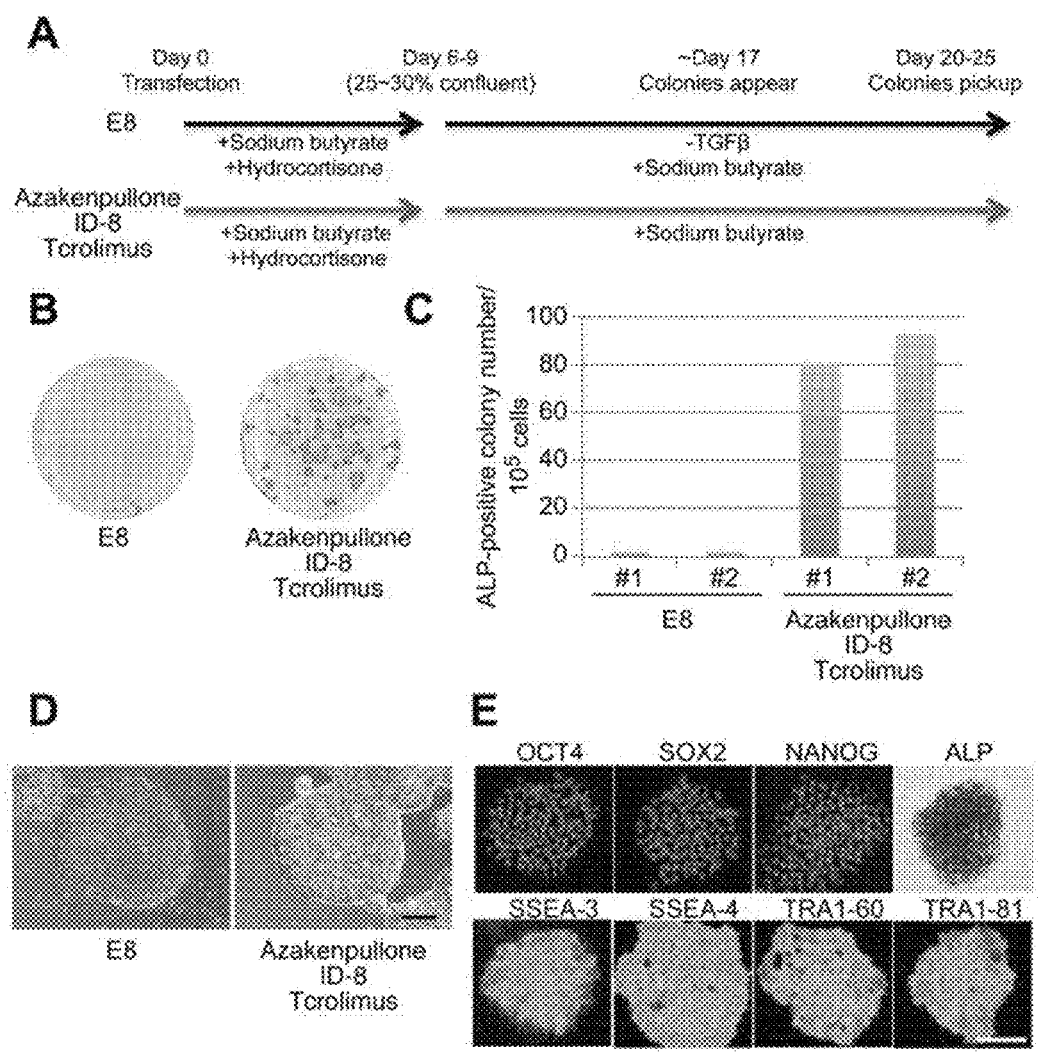
FIG. 9(A) shows the scheme for producing iPS cells of Example 8.
FIG. 9(B) shows images of ALP staining observed in Example 8.
FIG. 9(C) shows the iPS production efficiency as measured in Example 8.
FIG. 9(D) shows images of the iPS cells produced in Example 8.
FIG. 9(E) shows the results of immunostaining of Example 8.

Production of iPS Cells iPS cells were produced from human fetal fibroblasts (HDF-f, 2300, ScienCell), based on the methods disclosed in documents regarding iPS production (Nature Methods (2011) 8: 424-429, Nature Protocol 7 (2012): 2029-2040). FIG. 9A. shows its scheme. On Day 0, a reprogramming factor (OCT4, SOX2, KLF4, c-MYC, LIN28, and SV40LargeT) expression episomal vector (pEB-05 or pEB-Tg (Cell Research (2011) 21: 518-529)) was transfected into human fetal fibroblasts in accordance with a standard method. Subsequently, culture was performed until Day 6-9 in an E8 medium to which sodium butyrate (final concentration in the medium: 100 μM) and hydrocortisone (final concentration in the medium: 100 nM) had been added; or in the medium (Example 3) comprising a GSK3β inhibitor (1-azakenpaullone), a DYRK inhibitor (ID-8), and an NFAT inhibitor (tacrolimus) to which sodium butyrate (final concentration in the medium: 100 μM) and hydrocortisone (final concentration in the medium: 100 nM) had been added. From Day 6-9, hydrocortisone was removed from both of the media, TGFβ was further removed from the E8 medium, and culture was performed until Day 20-25. The cells in culture wells were stained with alkaline phosphatase (ALP) in accordance with a standard method, and the number of ALP-positive colonies was counted. The value obtained by dividing this counted value by the number of cells transfected with a reprogramming factor expression vector was considered to be the iPS cell production efficiency.

Observation of Form of Colonies and Confirmation of Undifferentiated Marker Expression After the production of iPS cells, colonies were picked up and cultured using an E8 medium or the medium (Example 3) comprising a GSK3β inhibitor (1-azakenpaullone), a DYRK inhibitor (ID-8), and an NEAT inhibitor (tacrolimus) for 60 days in accordance with a standard method. After the culture, images of the cells were observed. Further, the expression of undifferentiated markers (OCT4, SOX2, NANOG, ALP, SSEA-3, SSEA-4, TRA1-81, and TRA1-60) was detected by immunostaining as in Example 4.

Results

FIG. 9B shows images of ALP staining, FIG. 9C shows the iPS production efficiency, FIG. 9D shows the observation results of the form of colonies, and FIG. 9E shows the results of immunostaining. In FIG. 9C, #1 and #2 are the results of different wells.

FIGS. 9B and 9C indicate that the use of the medium of the present invention enabled the production of iPS cells much more efficiently (about 40 times more efficiently) than the existing media. Further, in view of FIGS. 9D and 9E, the iPS cells produced using the medium of the present invention had a normal form, and the expression of the undifferentiated markers was also confirmed.

The invention claimed is:

1. A culture medium comprising:
   (A) 1-azakenpaullone; and
   (B) a dual-specificity tyrosine-phosphorylation-regulated kinase (DYRK)1A inhibitor, a DYRK1B inhibitor, or a DYRK1A inhibitor and a DYRK1B inhibitor.

2. The medium according to claim 1, wherein the medium is free from serum.

3. The medium according to claim 1, wherein the medium is free from a differentiation-suppressing protein.

4. The medium according to claim 1, wherein the medium comprises only insulin and transferrin as protein components.

5. The medium according to claim 1, wherein (B) is at least one member selected from the group consisting of indole derivative-8 (ID-8), harmine, and indirubin analogs.

6. The medium according to claim 1, wherein (B) is ID-8.

7. The medium according to claim 1, wherein the medium comprises: (C) a nuclear factor of activated T-cells (NFAT) inhibitor.

8. The medium according to claim 7, wherein (C) is tacrolimus.

9. The medium according to claim 1, wherein the medium comprises at least one antioxidant agent.

10. The medium according to claim 9, wherein the at least one antioxidant agent comprises ascorbic acid.

11. The medium according to claim 1, wherein the concentration of the 1-azakenpaullone is 10 to 3000 nM.

12. A differentiation-suppressing agent for pluripotent stem cells, wherein the agent comprises:
   (A) 1-azakenpaullone; and
   (B) a DYRK1A inhibitor, a DYRK1B inhibitor, or a DYRK1A inhibitor and DYRK1B inhibitor.

13. A method for culturing pluripotent stem cells, wherein the method comprises using the medium of claim 1.

14. The method according to claim 13, wherein the method comprises culturing in the absence of feeder cells.

* * * * *